(12) United States Patent
Convert et al.

(10) Patent No.: US 11,131,044 B2
(45) Date of Patent: Sep. 28, 2021

(54) METHOD FOR PRODUCING A TUBULAR COMPRESSION ITEM, AND ITEM THEREBY OBTAINED

(71) Applicant: THUASNE, Levallois Perret (FR)

(72) Inventors: Reynaid Convert, Saint Martin la Plaine (FR); Aurélia Ruer, Saint Maurice en Gourgois (FR); Gérard Cattiaux, La Fouillouse (FR); Pascal Motet, Saint Etienne (FR)

(73) Assignee: THUASNE, Levallois Perret (FR)

( * ) Notice: Subject to any disclaimer, the term of this patent is extended or adjusted under 35 U.S.C. 154(b) by 627 days.

(21) Appl. No.: 14/426,793

(22) PCT Filed: Sep. 4, 2013

(86) PCT No.: PCT/FR2013/052039
§ 371 (c)(1),
(2) Date: Mar. 9, 2015

(87) PCT Pub. No.: WO2014/044945
PCT Pub. Date: Mar. 27, 2014

(65) Prior Publication Data
US 2015/0245951 A1   Sep. 3, 2015

(30) Foreign Application Priority Data
Sep. 19, 2012  (FR) ..................... 12 58771

(51) Int. Cl.
*A61F 13/08*    (2006.01)
*D04B 1/26*     (2006.01)
(Continued)

(52) U.S. Cl.
CPC .............. *D04B 1/265* (2013.01); *A61F 13/08* (2013.01); *D04B 1/106* (2013.01); *D04B 1/18* (2013.01); *D04B 15/18* (2013.01)

(58) Field of Classification Search
CPC ........... A61F 13/08; D04B 1/106; D04B 1/18; D04B 1/22; D04B 1/24; D04B 1/26;
(Continued)

(56) References Cited

U.S. PATENT DOCUMENTS 147,810 A  *  2/1874  Baron .................... A41D 17/00
                                                         2/240
323,287 A  *  7/1885  Appleton ................. D04B 1/26
                                                         2/240

(Continued)

FOREIGN PATENT DOCUMENTS

AT         206576 B   * 12/1959   ............... D04B 1/18
EP         0003498 A2   8/1979
(Continued)

*Primary Examiner* — Megan E Lynch
(74) *Attorney, Agent, or Firm* — MH2 Technology Law Group LLP

(57) ABSTRACT

The object of the present invention is a method for manufacturing a tubular compression item, having at least one leg part, one foot tip, one heel and one foot, comprising a first step for knitting the leg part and the foot with at least one knitting yarn on a double cylinder knitting machine during which an elastic weft yarn is inserted between two rows of ribbed stitches (n)*(p) and (n')*(p') every 1/1 to 1/5 rows of stitches of the leg part and of the foot, on at least 50% by number of the number (m) of needles without forming any tuck stitch or loop stitch.

13 Claims, 8 Drawing Sheets

(51) Int. Cl.
    *D04B 1/10*         (2006.01)
    *D04B 1/18*         (2006.01)
    *D04B 15/18*       (2006.01)

(58) Field of Classification Search
    CPC ........ D04B 1/265; D04B 15/00; D04B 15/14; D04B 15/18
    USPC .................................. 66/178 A, 178 R, 188
    See application file for complete search history.

(56) References Cited

U.S. PATENT DOCUMENTS

| | | | | |
|---|---|---|---|---|
| 672,028 | A * | 4/1901 | Appleton | D04B 1/24 2/109 |
| 1,110,443 | A * | 9/1914 | Kilbourn | D04B 1/26 66/186 |
| 1,577,752 | A * | 3/1926 | Price | D04B 1/26 2/61 |
| 1,795,131 | A * | 3/1931 | Lawson | D04B 1/26 66/182 |
| 1,863,719 | A * | 6/1932 | Lawson | D04B 9/18 66/188 |
| 1,890,299 | A * | 12/1932 | Mutchler | D04B 1/26 66/178 A |
| 1,979,233 | A * | 10/1934 | Smith, Jr. | D04B 1/26 66/182 |
| 2,054,059 | A * | 9/1936 | Longtin | D04B 9/54 66/172 E |
| 2,188,241 | A * | 1/1940 | Davis | D04B 1/26 66/172 E |
| 2,223,749 | A * | 12/1940 | Thurston | D04B 1/106 66/172 E |
| 2,301,065 | A * | 11/1942 | Mills | D04B 9/46 66/111 |
| 2,474,894 | A * | 7/1949 | Gottschalck | D04B 9/025 66/183 |
| 2,685,185 | A * | 8/1954 | Wagoner | D04B 9/06 66/13 |
| 2,739,467 | A * | 3/1956 | Stern | D04B 1/26 66/185 |
| 2,872,800 | A * | 2/1959 | Davis, Jr. | D04B 1/26 66/172 R |
| 3,015,943 | A * | 1/1962 | Loizillon | D04B 1/26 66/188 |
| 3,068,675 | A * | 12/1962 | Payne, Jr. | D04B 11/00 66/178 R |
| 3,301,018 | A * | 1/1967 | Knohl | D02G 3/322 57/225 |
| 3,386,270 | A * | 6/1968 | Simmons | A61F 13/08 2/240 |
| 3,402,575 | A | 9/1968 | Peberdy | |
| 3,763,668 | A * | 10/1973 | Williams | D04B 1/243 66/177 |
| 3,935,718 | A * | 2/1976 | Carminati | D04B 1/26 66/9 R |
| 3,946,577 | A * | 3/1976 | Townsend | D04B 9/10 66/14 |
| 3,995,322 | A * | 12/1976 | Chesebro, Jr. | A41B 11/00 2/239 |
| 4,015,448 | A * | 4/1977 | Knohl | D04B 9/52 66/178 A |
| 4,027,667 | A * | 6/1977 | Swallow | D04B 9/52 602/63 |
| 4,086,790 | A * | 5/1978 | Hanrahan, Jr. | D04B 1/265 66/178 A |
| 4,109,492 | A * | 8/1978 | Roberts | D04B 1/106 66/172 E |
| 4,125,001 | A * | 11/1978 | Bryars | D04B 1/04 66/190 |
| 4,172,370 | A * | 10/1979 | Safrit | D04B 1/02 66/178 R |
| 4,172,456 | A * | 10/1979 | Zens | A61F 13/08 2/240 |
| 4,180,065 | A * | 12/1979 | Bowen | A61F 13/08 2/239 |
| 4,237,707 | A * | 12/1980 | Safrit | D04B 1/18 66/172 E |
| 4,422,307 | A * | 12/1983 | Thorneburg | A41B 11/003 2/239 |
| 4,499,742 | A * | 2/1985 | Burn | D04B 1/26 66/172 E |
| 4,502,301 | A * | 3/1985 | Swallow | A61F 13/08 602/62 |
| 4,520,635 | A * | 6/1985 | Shields | A41B 11/02 2/239 |
| 4,561,267 | A * | 12/1985 | Wilkinson | D04B 1/26 66/172 E |
| 4,674,489 | A | 6/1987 | Lundy | |
| 4,732,015 | A * | 3/1988 | Abrams | A41B 11/02 66/172 E |
| 4,958,507 | A * | 9/1990 | Allaire | A41B 11/005 66/19 |
| 5,417,091 | A * | 5/1995 | Moser | A41B 11/00 2/239 |
| 5,509,282 | A * | 4/1996 | Ferrell, Jr. | A41B 11/005 2/239 |
| 5,540,063 | A * | 7/1996 | Ferrell | D04B 1/106 66/172 E |
| 5,617,745 | A * | 4/1997 | Della Corte | A41B 11/003 2/239 |
| 6,012,177 | A * | 1/2000 | Cortinovis | A61F 13/08 2/239 |
| 6,125,665 | A * | 10/2000 | Lonati | D04B 1/26 2/239 |
| 6,151,922 | A * | 11/2000 | Shimasaki | D04B 1/02 66/190 |
| 6,158,253 | A * | 12/2000 | Svoboda | A41B 11/004 2/239 |
| 6,216,495 | B1 * | 4/2001 | Couzan | A61F 13/08 2/239 |
| 6,341,506 | B1 * | 1/2002 | Myers | A41B 11/14 66/178 R |
| 6,430,970 | B1 * | 8/2002 | Gardon-Mollard | A61F 13/08 66/178 A |
| 6,502,430 | B1 * | 1/2003 | Myers | A41B 11/14 66/178 R |
| 6,684,412 | B2 * | 2/2004 | Ricci | A61F 13/08 2/240 |
| 6,725,691 | B2 * | 4/2004 | Yakopson | A61F 13/08 2/240 |
| 7,192,411 | B2 * | 3/2007 | Gobet | A61F 13/08 2/239 |
| 8,317,736 | B2 * | 11/2012 | Virkus | A61F 13/08 2/240 |
| 9,777,413 | B2 * | 10/2017 | Messier | D04B 9/52 |
| 2001/0013138 | A1 * | 8/2001 | Myers | A41B 11/14 2/239 |
| 2002/0029012 | A1 * | 3/2002 | Gardon-Mollard | A61F 13/08 602/62 |
| 2002/0152773 | A1 * | 10/2002 | Shibata | A41B 11/02 66/69 |
| 2006/0021390 | A1 * | 2/2006 | Gebel | A61F 5/0109 66/202 |
| 2006/0085894 | A1 * | 4/2006 | Yakopson | A61F 13/08 2/239 |
| 2007/0029308 | A1 | 2/2007 | Arabeyre et al. | |
| 2007/0033711 | A1 * | 2/2007 | Achtelstetter | A41B 11/00 2/239 |
| 2007/0113593 | A1 * | 5/2007 | Jeong | A41B 11/00 66/180 |
| 2007/0283483 | A1 * | 12/2007 | Jacober | A41B 11/00 2/239 |
| 2008/0249454 | A1 * | 10/2008 | Mills | A61F 13/08 602/63 |
| 2010/0005568 | A1 * | 1/2010 | Smith | A61F 13/08 2/240 |
| 2010/0130903 | A1 * | 5/2010 | Rock | A61F 13/06 602/62 |

(56) References Cited

U.S. PATENT DOCUMENTS

| | | | |
|---|---|---|---|
| 2010/0137776 A1* | 6/2010 | Virkus | A61F 13/08 602/62 |
| 2012/0035510 A1* | 2/2012 | Cros | A61F 13/08 600/592 |
| 2012/0078156 A1* | 3/2012 | Platz | A61F 13/08 602/76 |
| 2012/0116282 A1* | 5/2012 | Cros | A61F 13/08 602/76 |
| 2012/0324961 A1* | 12/2012 | Clemendot | A61F 13/08 66/178 R |
| 2013/0047313 A1* | 2/2013 | Windisch | A41D 13/0015 2/69 |
| 2013/0053744 A1* | 2/2013 | Convert | A61F 13/069 602/26 |
| 2013/0263629 A1* | 10/2013 | Gaither | A61F 13/08 66/185 |
| 2015/0051524 A1* | 2/2015 | Messier | A61F 13/08 601/84 |
| 2015/0245951 A1* | 9/2015 | Convert | A61F 13/08 66/178 A |
| 2016/0038346 A1* | 2/2016 | Collins | A61F 13/08 602/63 |
| 2017/0049631 A1* | 2/2017 | Slaski | A61F 5/0111 |
| 2017/0119585 A1* | 5/2017 | Gallien | A61F 13/085 |
| 2017/0319395 A1* | 11/2017 | Cros | A61F 13/08 |
| 2017/0370035 A1* | 12/2017 | Lonati | D04B 15/58 |

FOREIGN PATENT DOCUMENTS

| | | | | |
|---|---|---|---|---|
| EP | 0045287 A1 | | 2/1982 | |
| EP | 1621164 A1 | | 2/2006 | |
| EP | 1878822 A1 | | 1/2008 | |
| FR | 1428069 A | * | 2/1966 | D04B 1/26 |
| FR | 1450226 A | | 5/1966 | |
| FR | 2181324 A5 | | 11/1973 | |
| FR | 2255406 A1 | | 7/1975 | |
| FR | 2781816 A1 | | 2/2000 | |
| FR | 2852509 A1 | | 9/2004 | |
| FR | 2888855 A1 | | 1/2007 | |
| GB | 479120 A | * | 1/1938 | D04B 1/26 |
| GB | 786637 A | * | 11/1957 | D04B 1/265 |
| GB | 898983 A | * | 6/1962 | D04B 1/18 |
| GB | 951610 A | * | 3/1964 | D04B 1/18 |
| SU | 108059 A1 | | 11/1956 | |
| WO | WO-2011143489 A2 | * | 11/2011 | A61F 13/08 |
| WO | 2012/101618 A1 | | 8/2012 | |

* cited by examiner

METHOD FOR PRODUCING A TUBULAR COMPRESSION ITEM, AND ITEM THEREBY OBTAINED

BACKGROUND OF THE INVENTION

The present invention relates to the technical field of methods for manufacturing tubular compression items, in particular items exerting gradual compression from the ankle up to the top of the leg.

Compression items, socks or knee-length stockings, stockings, pantyhoses or further sleeves, are used for preventing or caring for venous circulation problems notably at the lower or upper limb, as well as pathologies related to malfunctions of the lymphatic system and reduction of edemas. Venous disorders may have several origins, among which are notably found: rigidification of the vein wall, alteration of the valvulae or further an increase in the diameter of the veins.

The local pressure exerted on a limb by an item with a compressive effect notably depends on the force-elongation characteristics of said item.

The pressure exerted on a limb is calculated by the following Laplace law:

$$P[\text{Pa or mmHg}] = (T[\text{N}] \times n)/(L[\text{m}] \times R[\text{m}]).$$

P represents the pressure exerted on a given point of the relevant limb.

L is the width of the relevant area of the limb and n represents the number of layers of the item with a compressive effect, positioned on said area.

T is the tension, expressed in Newtons, exerted by said item when it is slipped onto the lower or upper limb.

R is the radius of curvature at the relevant point of the lower or upper limb.

The greater the deficiency of the venous system, the more blood has difficulties for reflowing from the ankle back towards the heart, and the higher is the pressure to be exerted at the ankle.

As an example in the French system, the compression levels may be distributed in this way:

| Class I: 13 to 20 hPa | Class II: 20.1 to 27 hPa |
| --- | --- |
| Class III: 27.1 hPa to 48 hPa | Class IV: more than 48 hPa |

The compression items, notably of a high class, are difficult to slip on by the patient, notably when the latter suffers from reduced mobility.

Usually, medical compression stockings (or with a compressive effect) consist of two yarns, i.e. a weft yarn and a so-called knitting yarn. A weft yarn is an elastic yarn for which the travel is quasi-linear in the direction of the rows of stitches of compression items. The weft yarn gives the possibility of assigning the compressive effect to the compression item. The knitting yarn, also called background yarn gives the knitted compression item its dimensions as well as its comfort and esthetical properties.

In the state of the art, medical compression items are knitted on single-cylinder circular knitting machines with a transfer plate or on rectilinear machines with double needle bed, productivity being better with circular machines.

In the case of the production of a medical compression item on a single-cylinder knitting machine, the used knitting is generally of the plain stocking stitch type. In order that the weft yarn be secured to the knitted compression item, it produces tuck stitches or even sometimes loop stitches, on the knitting yarn, the weft yarn is then blocked in the feet of all or part of the knitted stitches with the knitting yarn.

When it is desired to assign a "rib" effect to the compression item, the knitting yarn or background yarn produces rows of knit stitches while the weft yarn produces tuck stitches with different ratios. The wider the ribbing, the more the float produced by the weft yarn on the back of the knit is also wide. These weft yarn floats being apparent on the back face of the knitted item form clinging areas and friction areas for the skin upon slipping on the item onto the leg thereby complicating its proper positioning.

The tuck stitch areas of the weft yarn form areas blocking the weft yarn in the transverse direction of the knitted tubular item limiting its elasticity, and make it even more difficult to put it into place and remove the compression item.

Thus there exists a need for a compression item not having any clinging and/or frictional areas with the skin and very easy to slip on while improving the comfort of said item.

Further, the finishing of the border or upper peripheral area downstream from the leg part of the compression item from which the foot is inserted into the item, involves blocking the knitting and weft yarns in order to avoid any fraying.

A first finishing technique quite simply consists of ending said upper peripheral area with sewing. This technique has the drawback that the back is not very esthetical and that it limits the elasticity of said area comparatively with the remainder of the compression item, which generates a border which does not remain in position on the leg, tends to slip and roll, and may prove to be uncomfortable.

A second technique consists of producing a welt by knitting at said upper peripheral area, said welt has a knitting weave close to the one of the remainder of the compression item but it is obtained by transferring stitches between the plate and the cylinder, more specifically between the transfer plates and the needles, thereby forming a double thickness. The thereby formed welt exerts greater pressure on the leg than the one exerted by the leg part. The welt may even, in certain cases, exert a tourniquet effect. This welt formed with double thickness is also warmer than the remainder of said compression item. Finally, according to the morphology of the patient, it tends to slip.

Therefore there exists a need for a tubular compression item exerting a compressive force on the ankle as far as the calf which is perfectly gradual and the border or peripheral area of which does not slip or roll on the leg and is not thicker, i.e. having a basis weight (g/m$^2$) which is not larger than that of the remainder of the compression item.

OBJECT AND SUMMARY OF THE INVENTION

The present invention overcomes all or part of the aforementioned problems in that it relates according to a first aspect to a method for manufacturing a tubular compression item, of the sock, stocking or knee-length stocking, or pantyhose type, having at least one leg part, a foot tip, a heel, a foot and a ribbed edge in the extension of the leg part delimiting an aperture for introducing the foot into said item, comprising the following steps:

a. a first step for knitting the leg part, the foot and the ribbed edge with at least one knitting yarn on a double cylinder knitting machine comprising an upper cylinder and a lower cylinder each operating with (m) needles, during which several rows of rib stitches (n)*(p), (n')*(p') and (n")*(p") are respectively knitted for the leg part, the foot and the rib edge (6); (m), (n), (n'), (n"), (p), (p') and (p") being integers greater than or equal to 1, b. an insertion step during the first step for knitting an elastic weft yarn between two rows of ribbed stitches (n)*(p) and (n')*(p') every 1/1 to 1/5 rows of stitches of the leg part and of the foot and every 1/2 to 1/5 rows of stitches of the ribbed edge, over at least 50% by number of the number (m) of needles without forming a tuck stitch, or a loop stitch, the weft yarn density on the ribbed edge being less than or equal to the weft yarn density in the leg part, c. a second step for knitting the foot tip and the heel on said double cylinder knitting machine with at least one knitting yarn and optionally an elastic weft yarn.

Advantageously, a double cylinder knitting machine gives the possibility of laying the weft yarn between two rows of consecutive stitches without blocking it by having it pass through the feet of the stitches so that the weft yarn is found between the knitted stitches on the location forming the outer face of the item and the knitted stitches on the back forming the inner face of the compression item. In the leg part and foot portions knitted with a knitting yarn along ribbed stitches and an elastic weft yarn, the weft yarn thus forms a somewhat intermediate layer positioned between the outer and inner faces and will not come directly into contact with the skin thereby avoiding the formation of clinging and/or frictional areas with the skin. Slipping on the item is thereby facilitated and the comfort of the contact of said item is improved.

Further, when the weft yarn is simply laid between two rows of consecutive stitches, it is not blocked in the feet of plain and/or purl stitches so that the elasticity of the thereby knitted areas is greater for a same compressive effect. This arrangement further improves comfort, facilitates slipping on and limits slip on the leg, of said item.

Finally, the ribs according to the invention are "real" ribbed stitches. Indeed, in the state of the art when a single cylinder knitting machine is used, the ribs are formed by bringing closer the weft yarn feeding areas, and therefore somewhat by puckering up the knitted areas positioned between these feed areas.

In the present text, the terms of "ribbed stitches" or "rib stitches" are used equally.

The weft yarn density corresponds to the insertion of a weft yarn every a/b rows of stitches, a and b being integers greater than or equal to 1.

Within the scope of the present invention, the leg part comprises several rows of rib stitches (n)*(p) while the foot and the ribbed edge comprise rows of ribbed stitches (n')*(p') and (n")*(p"), respectively, with n, n', n", p, p', and p" being integers greater than or equal to 1. Indeed, the ribbed structure may be different between the leg part, the foot and the ribbed edge. Also, the ribbed structure may be different in the actual inside of the leg part, of the foot and of the ribbed edge. Thus, as an example, the leg part may have ribbed 2/4 stitches alternating with ribbed 1/1 stitches.

The knitting yarn forms ribbed stitches, but may also form plain and/or purl jersey stitches depending on the sought effect.

The knitting machine used within the scope of the present invention is a double cylinder knitting machine, i.e. having an upper cylinder and a lower cylinder each operating with the same number of needles (m).

The weft yarn is preferably positioned between two rows of consecutive stitches over at least 50% by number of the number of worked needles (m), it may thus be tucked or looped depending on the sought effect over at most 50% by number of the remaining needles.

Preferably, the weft yarn is inserted between two consecutive rows of stitches on at least 75% of the number (m) of worked needles on the upper and lower cylinders, further preferably on at least 90% by number of the number (m) of worked needles, and still preferably on all the worked needles on the upper and lower cylinders without forming a tuck stitch or a loop stitch.

Advantageously, the double cylinder knitting machine gives the possibility of ending the insertion opening without resorting to a welt as this is the case with single cylinder machines. The ribbed edge does not have any fall back. In addition, the weft yarn density in the ribbed edge is less than the weft yarn density in the leg part which allows perfect gradual decrease of the exerted compression to be maintained and prevents the ribbed edge from exerting a tourniquet effect.

Said ribbed edge may comprise rows of plain and/or purl stitches, formed from the knitting yarn and optionally from the weft yarn inserted as a weft in the feet of stitches.

Preferably, the ribbed edge only comprises ribbed stitches (n")*(p"), which allows total suppression of the tendency of rolling of said opening and prevents slipping of the latter on the skin unlike a welt formed with jersey stitches.

Preferably, the elastic weft yarn is inserted between two rows of ribbed stitches every 1/2 to 1/5 rows of stitches over at least 75% by number, preferably over at least 90% by number of the number (m) of needles without forming any tuck stitch or loop stitch.

In a sub-alternative, the elastic weft yarn is inserted between two rows of ribbed stitches every 1/2 to 1/5 rows of stitches over all the worked needles (m) without forming any tuck stitch or loop stitch.

The tubular compressive item according to the invention has a longitudinal direction (L) and a transverse direction (T) corresponding to the columns of stitches and to the rows of stitches respectively.

Depending on the sought compressive force, the weft yarn may be inserted between all the rows of stitches or every 1/2 to 1/5 rows of stitches.

By an elastic yarn is understood a yarn having an elongation at break greater than or equal to 100%, preferably greater than or equal to 200%, and still preferably greater than or equal to 300%. These values may be determined by means of the NF EN ISO 2062 standard as of January 2010.

The assays indicated in the present text may be measured using the standard NF EN ISO 2060 of June 1995.

By tuck stitch is meant the arrangement of a yarn in a loop without this yarn itself forming a loop.

The knitting yarn according to the invention may be elastic.

In an alternative, the second knitting step does not comprise the weft insertion of an elastic weft yarn.

It is not necessary to exert a particular compression effect in the foot tip or the heel so that only the knitting yarn is knitted into these areas of the item.

In an alternative, the method according to the invention comprises, during said first step and/or said second step, a knitting sub-step with the knitting yarn in order to form one or several rows of loops plain and/or purl jersey stitches.

In an alternative, the ribbed edge has a height (h) of 1 mm at least.

Preferably, the ribbed edge has a height (h) of 20 mm at least and still preferably at least 50 mm.

In an alternative, the leg part has two consecutive distinct circular areas A and B. Further, during the first and second knitting steps, the tension exerted on the elastic weft yarn during the knitting of the area A is greater than the tension exerted on the elastic weft yarn in the area B so that the circumference of the circular area A is less than the circumference of the circular area B.

This arrangement advantageously allows formation of a leg part having a general frusto-conical shape for which the gradual decrease of the exerted compression is perfectly homogenous.

The exerted tension (daN) is the one applied on the weft yarn before its insertion into the upper or lower cylinder. This tension may be measured by means of a mechanical tensiometer.

In an alternative, the method according to the invention comprises during the first step and/or the second step, a sub-step during which the elastic weft yarn produces one or several tuck stitches.

In an alternative, the elastic weft yarn is inserted in the weft during the first step every 1/1 to 1/2 rows of stitches.

The object of the invention is also, according to a second aspect, a tubular item with a compressive effect, of the sock, stocking or knee-length stocking or pantyhose type, having at least one leg part, a foot tip, a heel and a foot, and a ribbed edge in the extension of the leg part delimiting an opening for introducing the foot into said item, obtained by applying the method according to any of the aforementioned alternative embodiments, comprising a ribbed knitted knitting yarn $(n)*(p)$, $(n')*(p')$ and $(n'')*(p'')$ respectively in the leg part, the foot and the ribbed edge, $(n)$, $(n')$, $(n'')$, $(p)$, $(p')$ and $(p'')$ being integers greater than or equal to 1, and an elastic weft yarn positioned between two rows of consecutive stitches every 1/1 to 1/5 rows of stitches in the leg part, the foot and the ribbed edge, over at least 50%, preferably over at least 75%, still preferably over at least 90%, by number of the number of columns of stitches without forming any tuck stitch, or loop stitch, the weft yarn density in the ribbed edge being less than or equal to the weft yarn density in the leg part.

In a sub-alternative, the elastic weft yarn is positioned between two rows of consecutive stitches every 1/1 to 1/5 rows of stitches in the leg part, the foot and optionally the ribbed edge over all the stitch columns without forming any tuck stitch or loop stitch.

In an alternative, the elastic weft yarn is inserted into the weft in the leg part and the foot every 1/1 to 1/2 rows of stitches.

In an alternative, the weft yarn consists of a yarn with an elastic core covered with one or several covering yarns, notably by reaming, said covering yarns preferably being non-elastic.

Preferably, the elastic core yarn is an elastane or elastodiene yarn.

In an alternative, the knitting yarn has a count comprised between 150 dtex and 2,000 dtex, preferably between 300 dtex and 1,500 dtex.

In an alternative, the knitting yarn has a count comprised between 15 dtex and 500 dtex, preferably between 20 dtex and 300 dtex.

The knitting yarn may consist of an elastic core yarn, notably an elastane yarn, covered with one or several covering yarns, notably by reaming, said covering yarns being preferably non-elastic.

In an alternative, the elastic weft yarn has a count at least three times greater than that of the knitting yarn, preferably at least five times greater than that of the knitting yarn.

This arrangement gives the possibility of adjusting the compressive effect exerted by said item.

In an alternative, the ribbed edge has a height (h) of at least 1 mm.

Preferably, the height (h) of the ribbed edge is greater than or equal to 20 mm, still preferably greater than or equal to 50 mm.

SHORT DESCRIPTION OF THE DRAWINGS

The present invention will be better understood upon reading an exemplary embodiment mentioned as non-limiting and illustrated by the following figures wherein:

FIG. 1 schematically illustrates a tubular compression item according to the invention, in particular a compression sock;

FIG. 2 schematically illustrates the knitting weave of the leg part and of the foot of the compressive sock illustrated in FIG. 1;

FIG. 3 schematically illustrates the knitting weave of the heel and of the foot tip of the compressive sock illustrated in FIG. 1;

Figure 1:
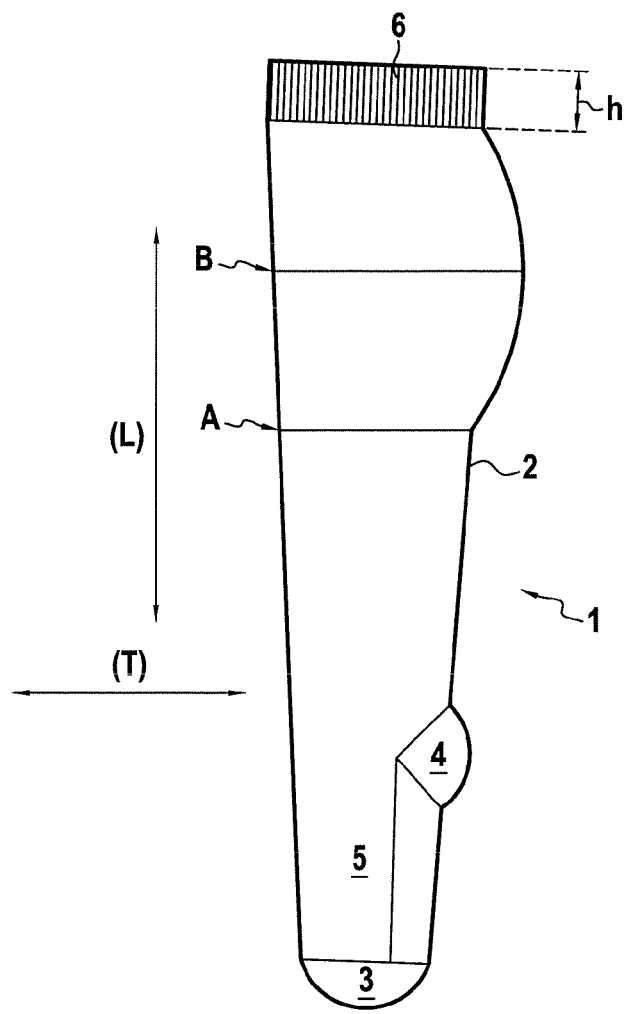
Figure 8:
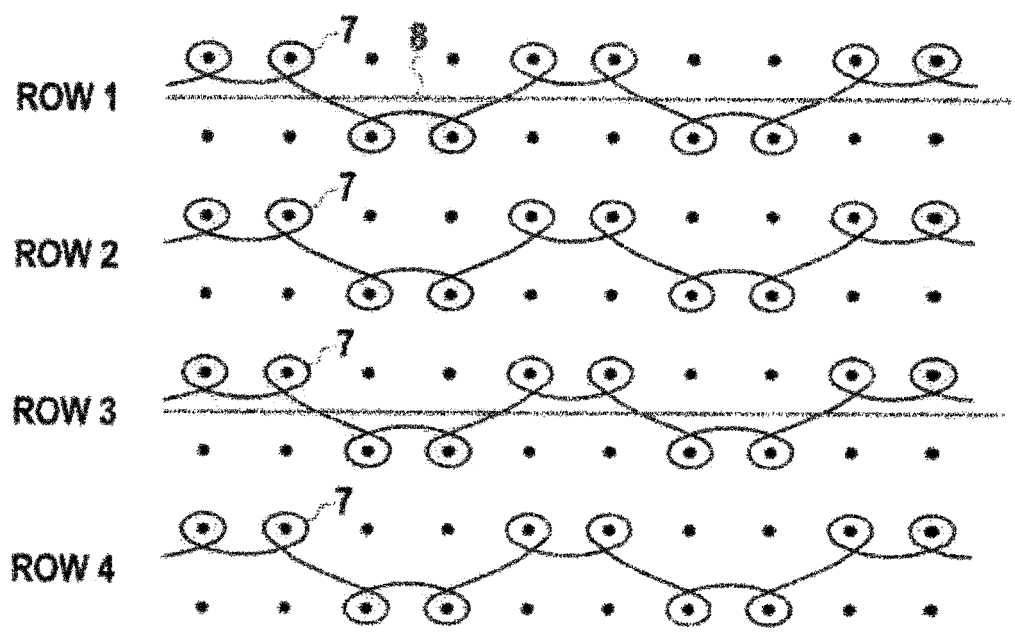

FIG. 8 schematically illustrates an example knitting weave of the leg part and of the foot of the compressive sock illustrated in FIG. 1.

DETAILED DESCRIPTION OF THE INVENTION

The tubular compression item 1 illustrated in FIG. 1 is a sock comprising a leg part 2, a foot tip 3, a heel 4, a foot 5 and a ribbed edge 6 in the extension of the leg part 2.

The whole of the item 1 is knitted on a double cylinder knitting machine, i.e. comprising upper and lower superposed cylinders each working with a determined number of needles (m).

The tubular item 1 comprises a longitudinal direction (L) and a transverse direction (T) corresponding to the direction of the columns of stitches and to the direction of rows of stitches respectively.

Figure 2:
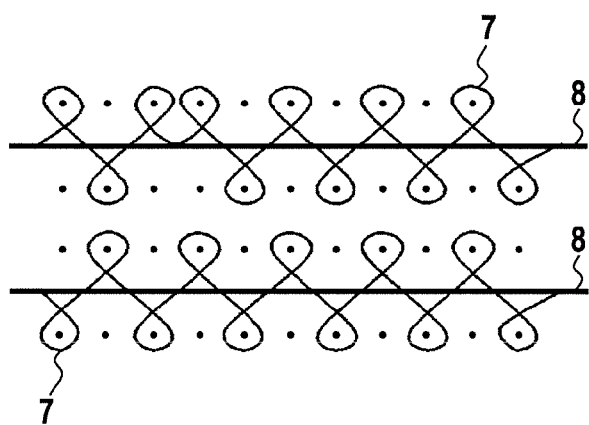

The leg part 2, the foot 5 and the ribbed edge 6 comprise several rows of ribbed stitches respectively $(n)*(p)$, $(n')*(p')$ and $(n'')*(p'')$ knitted with a knitting yarn 7 illustrated in FIG. 2, between which are inserted elastic weft yarn 8 every 1/1 to 1/5 rows of stitches. In this specific example, the elastic weft yarn 8 is inserted every 1/1 to 1/2 rows of ribbed stitches (n)*(p) and (n')*(p'), preferably between all the rows of ribbed stitches, in the leg part 2 and in the foot 5 without forming any tuck stitch or loop stitch on at least 50% by number of the number of worked needles (m), in this specific example without forming any tuck stitch or loop stitch on all the worked needles (m). The weft yarn density 8 is less significant in the ribbed edge 6 since the weft yarn 8 is preferably inserted every 1/2 or more rows of ribbed stitches (n")*(p").

The elastic weft yarn 8 may be inserted between two rows of ribbed stitches by forming a few tuck stitches according to the desired effect, preferably the weft yarn 8 does not form any tuck stitch and is simply laid between the needles of the upper cylinder and the needles of the lower cylinder.

Preferably, the ribbed edge 6, the leg part 2 and the foot 5 only comprise ribbed stitches, in particular the leg part 2 and the foot 5 comprise ribbed rows 2/4 alternating with rows of dimension 1/1, the knitting weaves are thus illustrated in FIG. 2.

Figure 3:
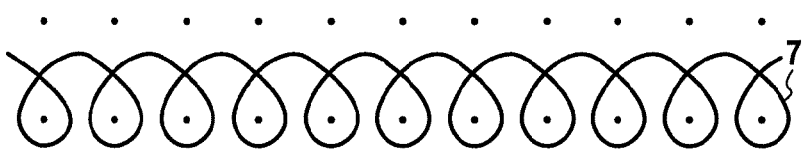

Preferably, the heel 4 and the foot tip 3 do not comprise an elastic weft yarn inserted in the weft and are knitted from the knitting yarn 8 according to jersey stitches, preferably knit jersey stitches, the knitting weave of which is illustrated in FIG. 3. The black dots illustrate in FIGS. 2 and 3 the needles of the upper and lower cylinders.

The leg part 2 comprises two consecutive circular areas A and B, the height of which is of the order of 5 mm.

As a specific example, the compression sock 1 according to the invention is knitted in its whole from the knitting yarn 7 comprising a yarn with an elastic core, in particular an elastane yarn of 44 dtex, covered with a first covering yarn, notably a yarn in polyamide 6-6 with two ends of 78 dtex each, and a second covering yarn, notably in cotton at one end of 120 Nm; and a weft yarn 8 (only for the leg part, the foot and the ribbed edge), comprising a yarn with an elastic core, in particular an elastane yarn of 330 dtex, covered with a first covering yarn, notably a polyamide yarn at an end of 22 dtex, and a second covering yarn, notably in cotton at an end of 160 Nm.

With the purpose of testing the elasticity performances of the compression sock according to the invention, a sock from the state of the art is knitted on a single cylinder knitting machine (i.e. cylinder-transfer plate, also designated under the term of «cylinder-dial») so as to substantially have the same dimensions, i.e. the same size, for the same medical compression class, i.e. class II as well as a welt formed with a double thickness. The compression sock of the state of the art is thus knitted from a knitting yarn comprising a yarn with an elastic core, in particular an elastane yarn of 22 dtex, covered with a first covering yarn, notably at an end of 78 dtex in polyamide 6-6 and with a second covering yarn, notably in cotton at an end of 160 Nm; and a weft yarn comprising a yarn with an elastic core, notably an elastane yarn of 330 dtex, covered with a first covering yarn, notably in polyamide 6-6 at an end of 22 dtex and of a second covering yarn, notably in cotton at an end of 160 Nm for the welt, the leg part and the foot. For the foot tip and the heel, the sock of the state of the art does not comprise any elastic weft yarn but a knitting yarn comprising a yarn with an elastic core, in particular an elastane yarn of 78 dtex, covered with a first covering yarn, notably a yarn in polyamide 6-6 at an end of 78 dtex, and with a second covering yarn, notably a cotton yarn at an end of 160 Nm. In order to produce a ribbed leg part and foot, the knitting yarn is knitted with a stocking stitch while the weft yarn produces tuck stitches with ratios of 1/2, 1/3 and 2/3.

Figure 4:
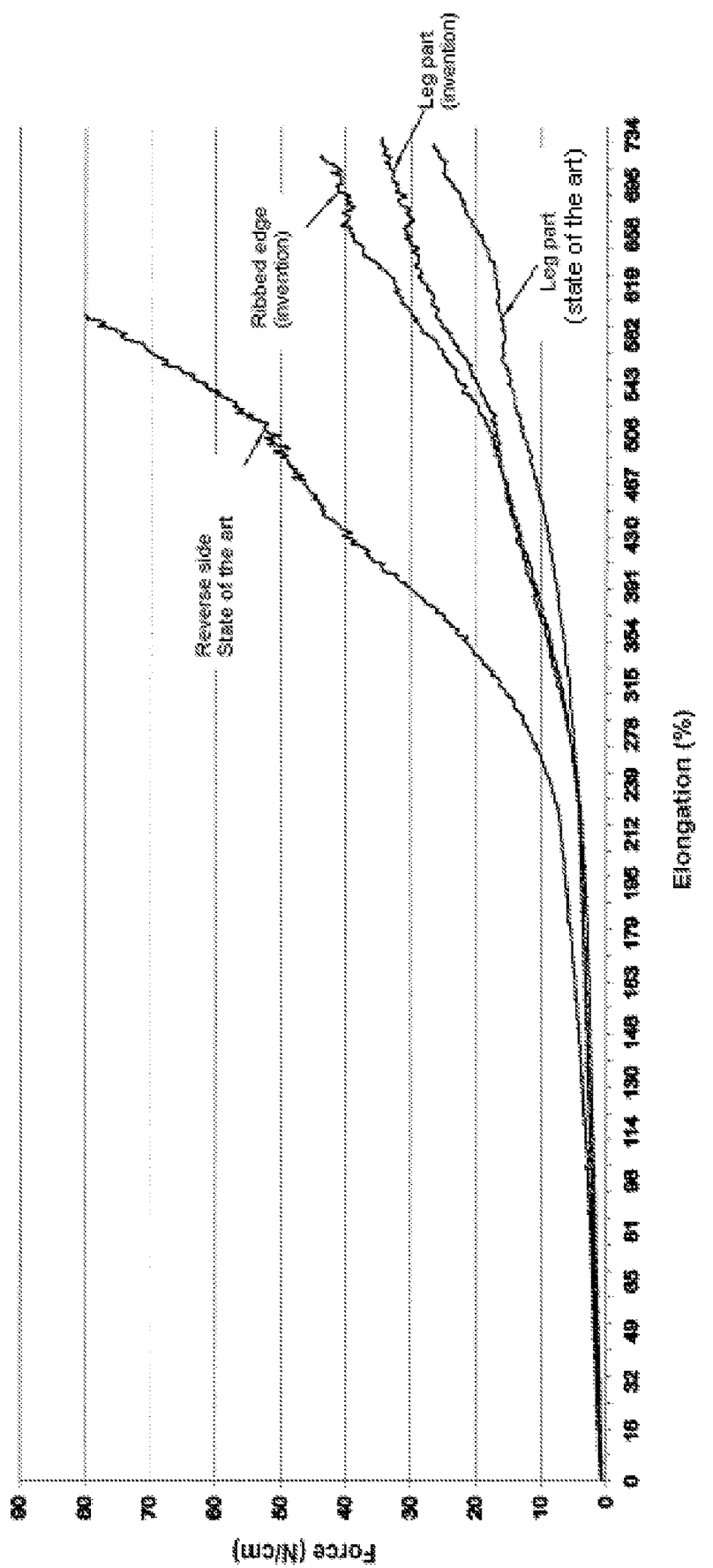
FIG. 4 illustrates a graph comparing the forces and elongations at break obtained for the leg part and for the ribbed edge of the item described in FIG. 1 with the forces and elongations at break of the leg part and of the welt of a compressive item of the state of the art, said compressive items being classified as belonging to the medical compression class II.
Figure 5A:
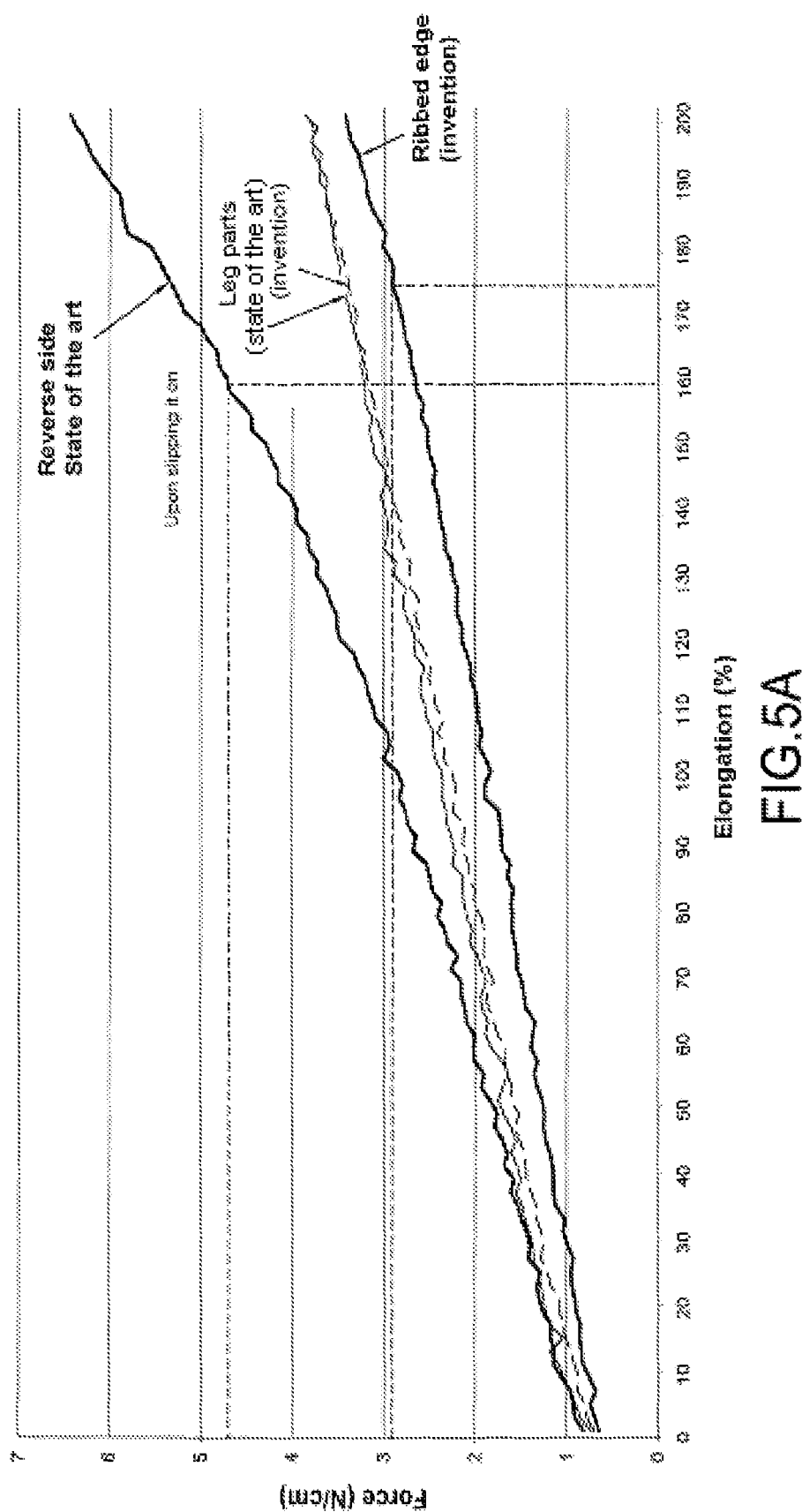
FIG. 5A illustrates curves comparing the forces to be applied for slipping on a compressive item according to the invention and a compressive item of the state of the art.
Figure 5B:
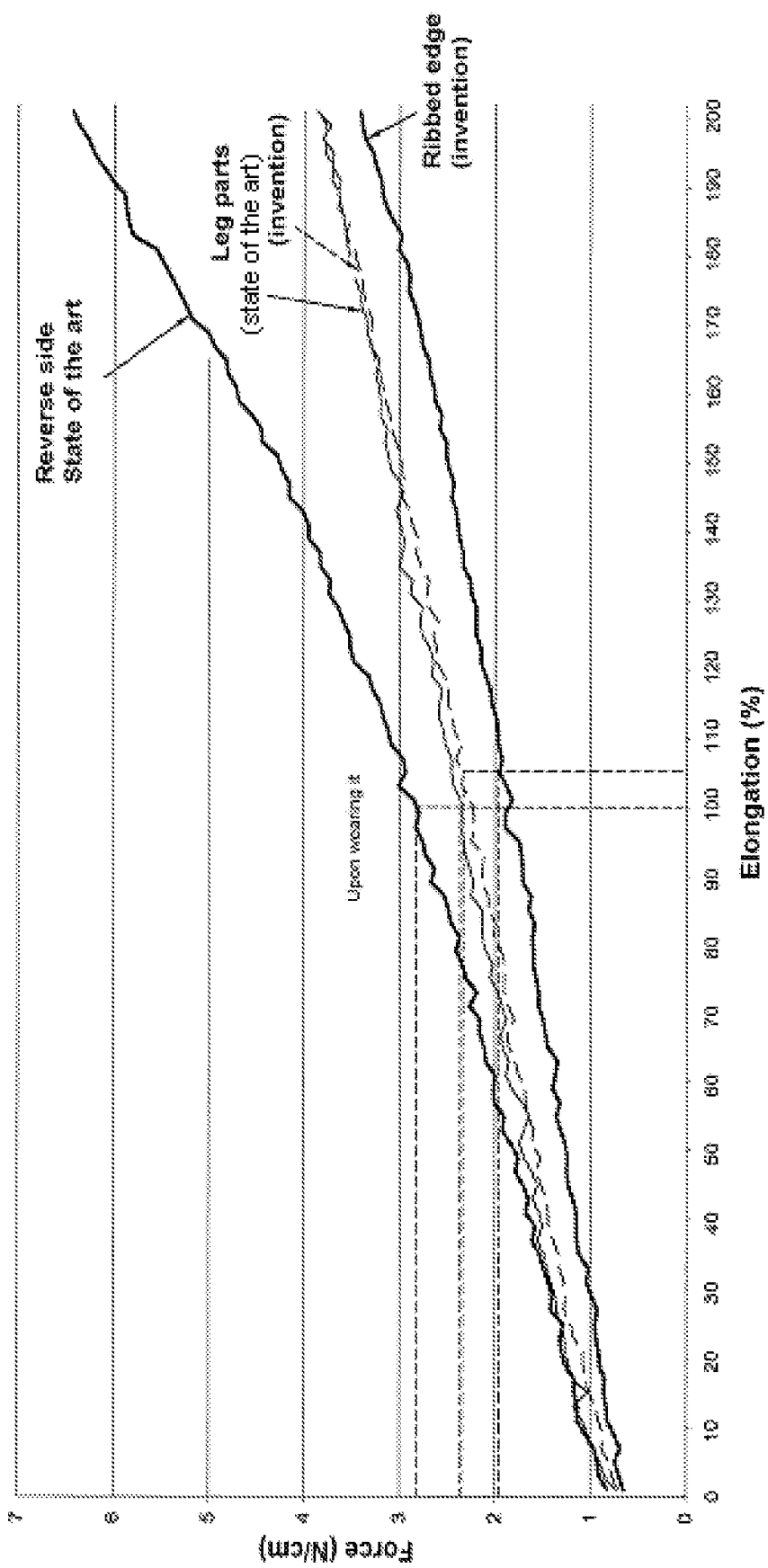
FIG. 5B illustrates curves comparing the forces and elongations obtained when the compressive item according to the invention and a compressive item of the state of the art are worn.

The curves of forces and elongations illustrated in FIGS. 4, 5A and 5B resume the measurement values conducted according to the NF 14-704-1 standard of June 2005. The compression forces at the ankle exerted by the compression sock according to the invention and by the sock of the state of the art are equivalent and measured according to the NF G30-102 B standard as of October 1986. The flat width at rest of the sock 1 according to the invention measured at the beginning of the ribbed edge on the leg part is 95 mm; it is 90 mm as regards the width at the beginning of the reverse side on the leg part of the compression sock of the state of the art. The compression socks to be tested are positioned on a Hohenstein leg so that they are in compliance with their placement upon wearing. On each of the socks, the height of the ribbed edge (h1) and the height of the welt (h2) are measured and transferred under the latter on the leg part. Annular ribbed edge and welt strips as well as leg part strips, respectively with a height (h1) and (h2) are cut out in each compression sock. These annular strips are open so as to form rectangular test specimens, the widths of which correspond to the wearer heights (h1) and (h2). Each of these specimens are placed on a force gauge and evaluated according to the aforementioned NF 14-704-1 standard. The gap between the jaws of the force gauge was adjusted to 50 mm.

The measurement of the forces and elongations is carried out in compliance with the wearing behavior of the compression socks; thus the welt is tested in a double thickness while the ribbed edge and the leg part strips are tested in a single thickness.

It is thus noted that the ribbed edge 6 has a greater elongation at break (about 716%) than that of the welt of the state of the art (about 596%). Moreover, the elastic behaviors of the leg part of the sock of the state of the art and of its welt diverge; the tourniquet effect of the criticized welt is thus again found. On the contrary, the elastic behaviors of the ribbed edge and of the leg part of the sock according to the invention are very close (respectively 716% and 728% of elongations at break) thus allowing very homogenous gradual decrease in the exerted compression to be obtained.

It is also noted that the force at breakage of the leg part of the compression sock according to the invention (34.5 N/cm) is greater by 29% than the force at breakage of the leg part of the sock of the state of the art (26.7 N/cm). A non-exhaustive explanation of this effect is that the elastic weft yarns do not form any tuck stitch or loop stitch, in the compression sock according to the invention, or optionally very few tuck stitches, while in the sock of the state of the art, the weft yarns form tuck stitches at very regular intervals, said tuck stitches forming anchoring and therefore blocking points of the stitched structure.

Table 1 below resumes values extracted from FIGS. 5A and 5B illustrating the behavior of the compression socks according to the invention and of the state of the art according to the ranges of use, i.e. upon wearing under an elongation ranging from 100% to 105% and upon slipping them on under an elongation ranging from 160% to 175%.

It is thus noted that two different elongations are transferred onto FIGS. 5A and 5B since the width of the tested areas at rest are different for the compression item according to the invention (90 mm) and the compression item of the state of the art (95 mm). These differences in lengths are due to the knitting machines used: either with one cylinder or two cylinders.

TABLE 1

|  |  | Sock of the state of the art | Sock according to the invention |
|---|---|---|---|
| At rest |  |  |  |
|  | Ribbed edge or welt width (mm) | 95 | 90 |
|  | Circumference (mm) | 190 | 180 |
| Upon wearing | Elongation (%) | 100 | 105 |
|  | Ribbed edge or welt force (N/cm) | 2.88 | 2.03 |
|  | Leg part force (N/cm) | 2.34 | 2.35 |
| Upon slipping them on | Elongation (%) | 160 | 175 |
|  | Ribbed edge or welt force (N/cm) | 4.72 | 2.86 |
|  | Leg part force (N/cm) | 3.18 | 3.38 |

The required force (N/cm) for slipping on the ribbed edge is less than 65% of that required for slipping on the welt of the compression sock of the state of the art. When the compression sock according to the invention is worn, the ribbed edge exerts a 16% less force (N/cm) than that exerted by the leg part, the gradual decrease of the exerted compression is thus perfectly observed. On the contrary, for the compression sock of the state of the art, the welt exerts a force (N/cm) 23% greater than that exerted by the leg part, the gradual decrease of the exerted compression is thus not perfectly ensured. Of course, because of the morphology of the leg, the radius of curvature being greater at the portion of the leg part covering the leg than that of the portion of the leg part covering the ankle, a global gradual decrease of the exerted compression is obtained all the same between the ankle and the leg. However, this gradual decrease is not perfectly regular and therefore homogenous between the ankle and the leg.

The compression sock according to the invention gives the possibility of improving comfort by preventing that the weft yarn forms significant floats on the reverse face of said sock, the latter arrangement combined with a ribbed edge also facilitates the slipping on of said sock 1.

Figure 6:
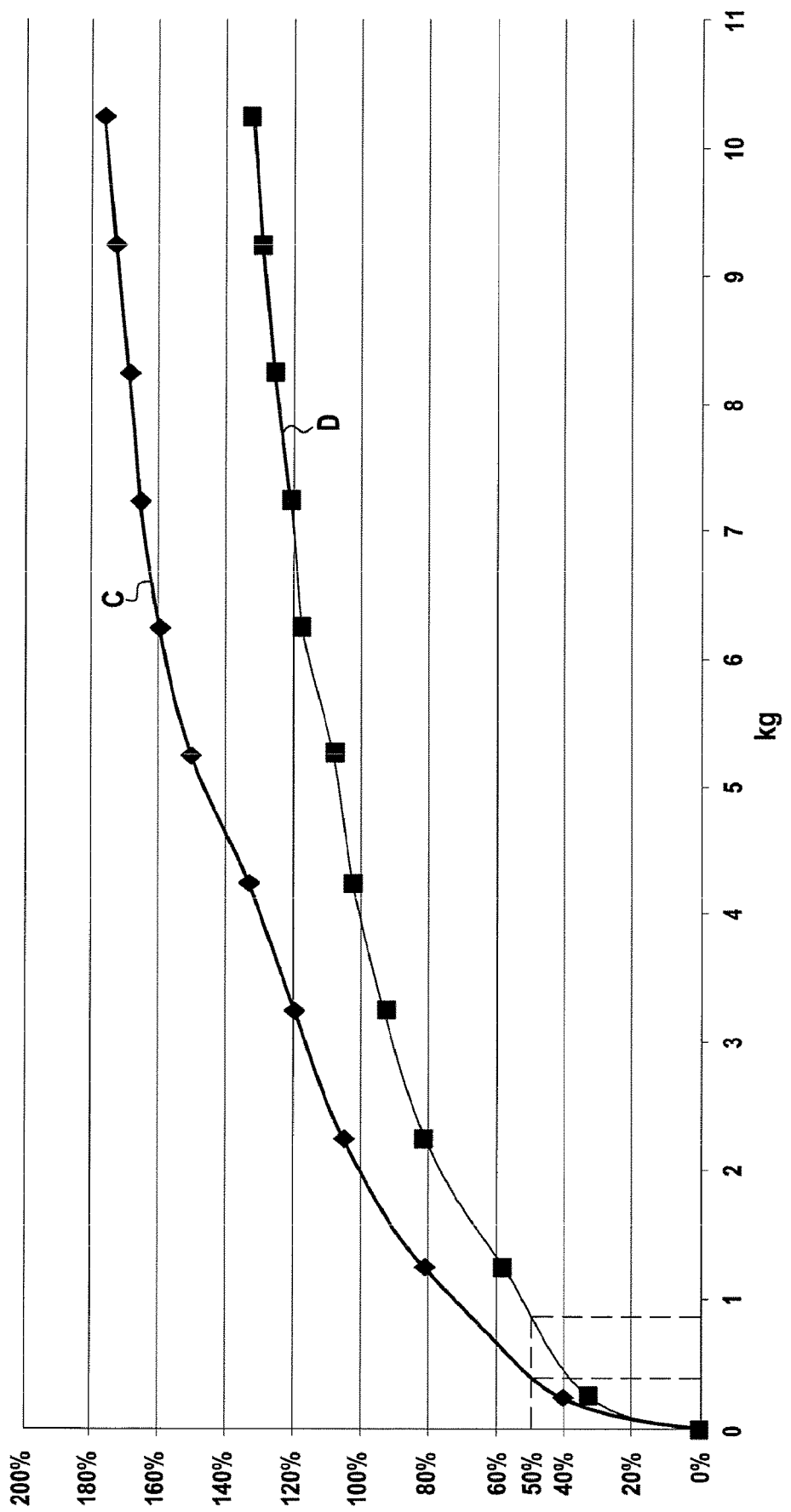
FIG. 6 illustrates two curves comparing the elongations obtained under the effect of a determined weight for a compressive item according to the invention (curve (C)), and a compressive item of the state of the art (curve (D))

FIG. 6 illustrates two curves (C, D) obtained by the extensibility test method described hereafter conducted on the leg parts of the compression sock 1 according to the invention and on the compression sock of the state of the art tested with reference to FIGS. 4, 5A and 5B, both having a compression level of class II.

The two tested socks have the same leg part height between the heel and the beginning of the welt or of the ribbed edge, i.e. 21 cm. Both socks also have the same size, the circumference at the ankle is 27.5 cm and the circumference at the calf is 41.5 cm. The height of the socks is 44 cm.

The socks are suspended on an extension bench by means of a first clamp clamping the socks on the leg part at the beginning of the welt or of the ribbed edge. A second clamp, movable relatively to the extension bench, is secured to the socks in the lower portion of the leg parts at the demarcation of the heel. Weights are hooked up on the second clamp so as to cause extension in the vertical direction of the leg parts of said socks. The extension bench is provided with a graduation allowing measurement of the obtained elongation according to the total weight applied at the second clamp.

The mass of the second clamp is 0.250 kg and the mass of each weight is 1 kg. The measurement of the extension of the leg parts is noted for the second clamp alone, and then by gradually adding a weight of 1 kg up to a total weight of 10 kg.

It is considered that when the compression socks are worn by the user, the leg parts are stretched by at least 50% of their lengths at rest.

Thus, in FIG. 6 it is observed that for an elongation of 50%, the force (kg) to be exerted for bringing the leg part to its application size is less for the compression sock according to the invention than the one required for the compression sock of the state of the art. Now, this force (kg) is also the one which is applied to the ribbed edge or to the welt when the compression sock is placed on the leg. The force or traction exerted by the compression sock according to the invention in the transverse direction (T) is about equal to 50% of the force exerted on the compression sock of the state of the art for a same elongation (%).

Thus, the conclusion may be drawn that the compression sock obtained by the method according to the invention has a better hold on the leg than the compression sock of the state of the art. Indeed, the compression sock according to the invention will have much less tendency to slip on the leg than the compression sock of the state of the art. This technical effect is explained by the design of the compression sock according to the invention, which comprises a freely positioned weft yarn between two consecutive rows of stitches, at least on 50% by number of the number (m) of the knitted needles without forming any tuck stitch or loop stitch. Maintaining a compression sock in place when it is worn is a balance between the compression exerted transversely and the elongation exerted by the leg on the sock between the ribbed edge or welt of the sock and the ankle.

The histograms illustrated in FIGS. 7A to 7D resume measurements conducted on compression socks according to the invention and of the state of the art described above and of class II according to the measurement method described hereafter. The measurements are conducted on the ribbed edge of the sock according to the invention (single thickness) and on the welt (double thickness) of the sock of the state of the art.

The weight composition of said socks is substantially equivalent:
  47% cotton, 43% polyamide and 10% elastane for the sock according to the invention,
  50% cotton, 38% polyamide, 12% elastane for the sock of the state of the art.

The compression socks were washed so as to remove all the residues stemming from the production methods. The sock specimens were taken on a standardized leg of the Hohenstein type.

The specimens, during the measurements, were stretched by at least 50% of their length at rest, which corresponds to the behavior of compression socks when they are worn.

This test method thus has the purpose of studying the dynamics of the transfer of steam through a textile part which has been put into contact beforehand with a known amount of water, in particular 1 mg of water, which corresponds to a drop of sweat. The flow density of steam evolved by the tested specimen is measured and studied over time. The device on which the test is conducted comprises a heating support heated to a temperature corresponding to the body temperature (35° C.), a sample holder, and a measurement cell, such as a Peltier measurement cell equipped with a regulator. The support, mounted facing the specimen holder, is preferably in copper and may be covered with a latex layer so as to reproduce human skin. The specimen holder is made so as to ensure the seal of the assembly formed with the support, the specimen and the measurement cell. Thus, ambient humidity and temperature variations do not have any incidence on the measurement. The measurement cell comprises a flowmeter and a condenser allowing discharge of humidity.

The time-dependent change in the flow density of steam through the specimens comprises the following steps: putting the specimen into contact with a drop of water corresponding to the absorption phase, a phase for transferring humidity into the specimen or diffusion phases followed by evaporation and drying phases.

Figure 7A:
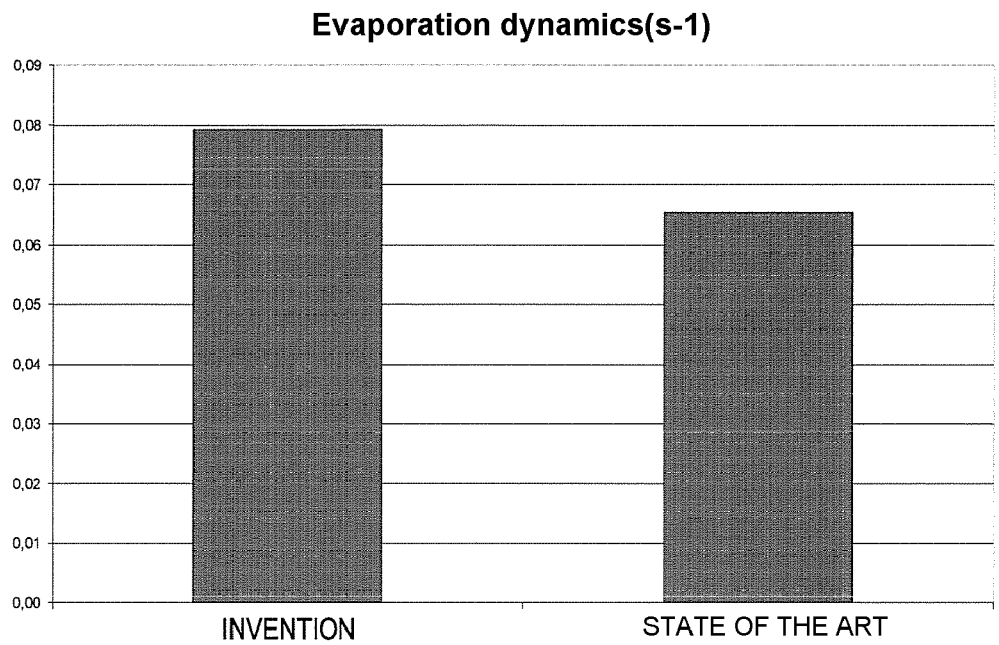
FIGS. 7A to 7D illustrate histograms comparing the humidity absorption properties (FIG. 7A), humidity removal properties (FIG. 7B), drying properties (FIG. 7C), and humidity retention properties (FIG. 7D) between compressive socks according to the invention and according to the state of the art described above with reference to FIGS. 1 to 6.
Figure 7B:
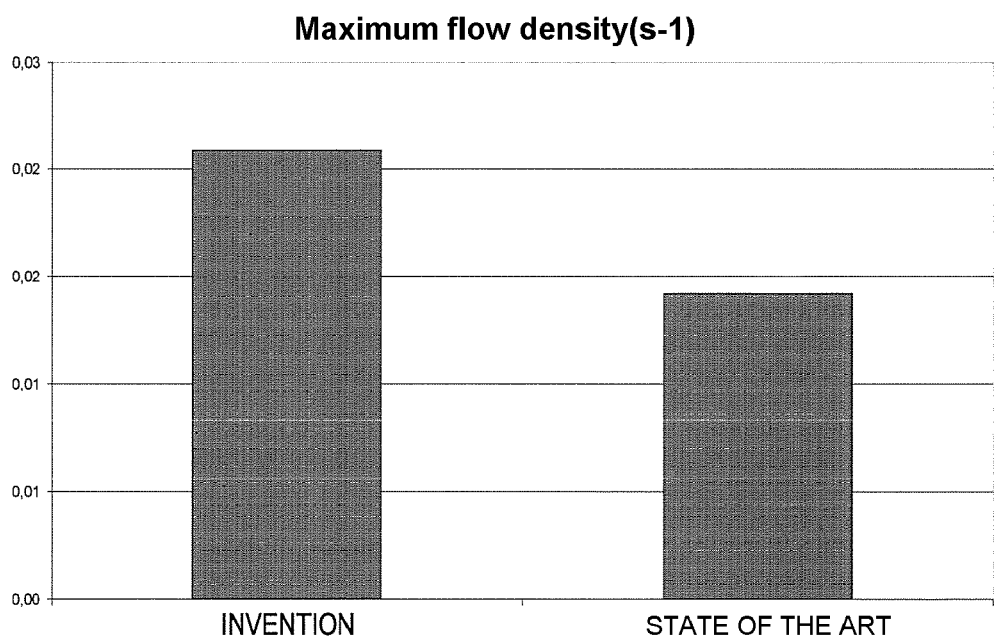
Figure 7C:
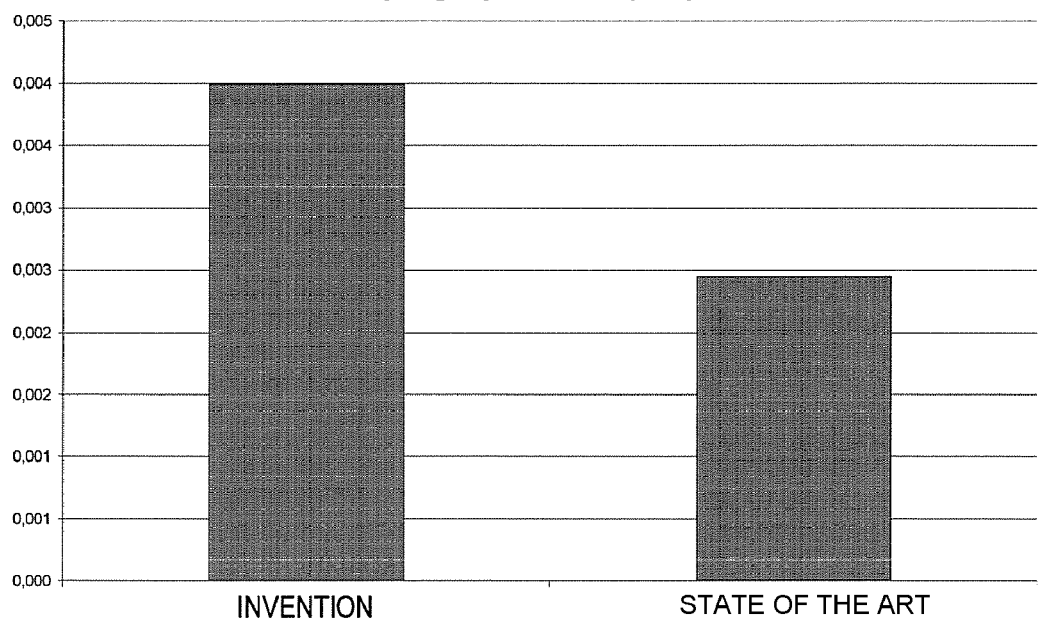
Figure 7D:
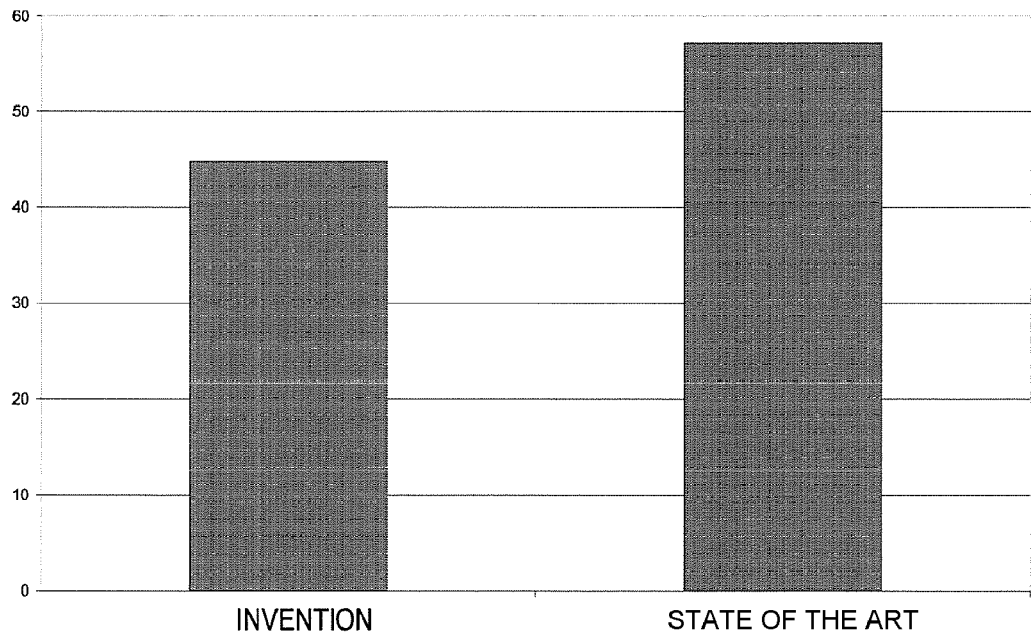

FIG. 7A corresponds to the humidity absorption phase during the putting into contact of the specimens with a drop of water. FIGS. 7B and 7C respectively correspond to the capability of the specimens to discharge the humidity based on the maximum steam flow density and the drying dynamics. Finally, FIG. 7D corresponds to the retention rate of the amount of water maintained in the specimens after the test, i.e. after their drying.

Upon reading these histograms, one notices that the compression sock according to the invention is superior in all points to the compression sock of the state of the art. The ribbed edge of the compression sock according to the invention thus absorbs more rapidly humidity, discharges it and dries more rapidly than the welt of the compression sock of the state of the art. Further, the ribbed edge of the compression sock according to the invention finally retains less humidity than the welt of the sock of the state of the art once the test is completed.

As a conclusion, the sock according to the invention significantly improves the thermal comfort of the user.

The invention claimed is:

1. A method for producing a tubular compression item, of a compression sock, compression stocking or compression knee-length stocking, or compression panty hose type having at least one leg part, one foot tip, one heel, one foot and one ribbed edge in the extension of the leg part delimiting an opening for introducing the foot into said item, said leg part having a height extending from the foot part up to the ribbed edge, comprising the following steps:

a first step for knitting the leg part, the foot and the ribbed edge of the tubular compression item with at least one knitting yarn on a double cylinder knitting machine comprising an upper cylinder and a lower cylinder each operating with (m) needles, wherein the leg part comprises rows of n*p ribbed stitches and has inner and outer faces, the foot comprises rows of n'*p' ribbed stitches and has inner and outer faces, and the ribbed edge comprises rows of n"*p" ribbed stitches and has inner and outer faces, (m), (n), (n'), (n"), (p), (p') and (p") being integers greater than or equal to 1, wherein each of the leg part, the foot and the ribbed edge of the tubular compression item comprise rows of stitches and columns of stitches;

a step for inserting, during the first knitting step, an elastic weft yarn between: the knitted stitches on the outer face and the knitted stitches on the inner face of the leg part in every row to every five rows of stitches over all the leg part's height; the knitted stitches on the outer face and the knitted stitches on the inner face of the foot in every row to every five rows of stitches in the foot; and the knitted stitches on the outer face and the knitted stitches on the inner face of the ribbed edge in every two rows to every five rows of stitches in the ribbed edge, wherein the elastic weft yarn is inserted, on at least 90% of the columns of stitches in the leg part, the foot and the ribbed edge, for one row of stitches, without forming any tuck stitch, or loop stitch, an elastic weft yarn density in the ribbed edge being less than or equal to a weft yarn density in the leg part, the elastic weft yarn density being the insertion of the elastic weft yarn every b rows of stitches, b being an integer greater than or equal to 1, wherein the elastic yarn is disposed and maintained between two consecutive rows of stitches in the leg part; and a second step for knitting the foot tip and the heel on said double cylinder knitting machine with at least one knitting yarn, wherein the elastic weft yarn has a count at least three times greater than the count of the knitting yarn, and wherein the leg part, the foot part, and the ribbed edge are of the same knitting pattern and comprise only ribbed stitches, and wherein the leg part comprises a circular area A and a circular area B, wherein the circular area A and the circular area B are consecutive and distinct, and during the first knitting step, the tension exerted on the elastic weft yarn during the knitting of the circular area A is greater than the tension exerted on the elastic weft yarn in the circular area B, so that the circumference of the circular area A is less than the circumference of the circular area B, and the leg part has a frusto-conical shape.

2. The production method according to claim 1, wherein the second knitting step does not comprise the weft insertion of an elastic weft yarn.

3. The production method according to claim 1, comprising during said first step, a sub-step for knitting the knitting yarn in order to form one or several rows of plain and/or purl jersey stitches.

4. The production method according to claim 1, wherein the ribbed edge has a height (h) at least of 1 mm.

5. The production method according to claim 1, comprising during the first step a sub-step during which the elastic weft yarn produces one or several tuck stitches.

6. The production method according to claim 1, wherein the elastic weft yarn is inserted during the first step every row to every two rows of stitches.

7. The production method according to claim 1, wherein during the second step for knitting the foot tip and the heel on said double cylinder knitting machine comprises the knitting of an elastic weft yarn.

8. The production method according to claim 1, comprising, during said second step, a sub-step for knitting the knitting yarn in order to form one or several rows of plain and/or purl jersey stitches.

9. The production method according to claim 1, wherein the elastic weft yarn is inserted during the first knitting step on at least 90% of the columns of stitches in the leg part, the foot and the ribbed edge, for one row of stitches, without forming any tuck stitch, or loop stitch.

10. The production method according to claim 1, wherein the elastic weft yarn is inserted as a weft in the leg part and the foot every row to every two rows of stitches.

11. The production method according to claim 1, wherein the weft yarn consists of a elastane yarn covered with at least two yarns.

12. The production method according to claim 1, wherein the elastic weft yarn has a count comprised between 150 dtex and 2,000 dtex.

13. The production method according to claim 1, wherein the knitting yarn has a count comprised between 15 dtex and 500 dtex.

* * * * *